United States Patent [19]
Chodorow

[11] Patent Number: 5,911,229
[45] Date of Patent: Jun. 15, 1999

[54] DENTAL FLOSSING DEVICE

[75] Inventor: Ingram S. Chodorow, Upper Saddle River, N.J.

[73] Assignee: Placontrol, Inc., Rancho Santa Fe, Calif.

[21] Appl. No.: 08/880,134

[22] Filed: Jun. 20, 1997

[51] Int. Cl.⁶ ................................................. A61C 15/00
[52] U.S. Cl. .......................................... 132/323; 132/321
[58] Field of Search ..................... 132/321, 323, 132/324, 325, 326, 327, 328, 329

[56] References Cited

U.S. PATENT DOCUMENTS

| | | | |
|---|---|---|---|
| D. 244,376 | 5/1977 | Chodorow | D28/64 |
| D. 250,214 | 11/1978 | Chodorow | D28/64 |
| 817,050 | 4/1906 | De La Cour | |
| 2,702,555 | 2/1955 | De Mar | 132/323 |
| 2,736,327 | 2/1956 | Schlicksupp | 132/323 |
| 3,696,821 | 10/1972 | Adams, IV | 1321/91 |
| 3,799,177 | 3/1974 | Bragg | 132/92 |
| 3,831,611 | 8/1974 | Hendricks | 132/92 R |
| 4,006,750 | 2/1977 | Chodorow | 132/91 |
| 4,016,892 | 4/1977 | Chodorow | 132/91 |
| 4,050,470 | 9/1977 | Miller | 132/323 |
| 4,403,625 | 9/1983 | Sanders et al. | 132/323 |
| 4,519,408 | 5/1985 | Charatan | 132/89 |
| 4,633,892 | 1/1987 | Charatan | 132/321 |
| 4,729,392 | 3/1988 | Tenny | 132/323 |
| 4,827,952 | 5/1989 | Kos | 132/323 |
| 4,836,227 | 6/1989 | Charatan | 132/324 |
| 4,986,289 | 1/1991 | McWhorter | 132/323 |
| 5,086,792 | 2/1992 | Chodorow | 132/323 |
| 5,174,314 | 12/1992 | Charatan | 132/328 |
| 5,538,023 | 7/1996 | Oczkowski et al. | 132/323 |

FOREIGN PATENT DOCUMENTS

| | | | |
|---|---|---|---|
| WO 88/07354 | 6/1988 | United Kingdom | 132/323 |

*Primary Examiner*—Gene Mancene
*Assistant Examiner*—Pedro Philogene
*Attorney, Agent, or Firm*—Ostrolenk, Faber, Gerb & Soffen, LLP

[57] ABSTRACT

A dental flossing device having a strand of dental floss, a gripping element attached to each end of the floss and at least one structural element for engaging and maintaining the gripping elements in fixed spatial relation relative to each other or the elements being releasably secured to each other, with the dental floss extended generally linearly between the gripping elements, each gripping element being breakable apart from the other or from the structural element for rendering the gripping elements freely movable relative to each other with the floss freely extendible or bendable between the gripping elements.

25 Claims, 7 Drawing Sheets

DENTAL FLOSSING DEVICE

BACKGROUND OF THE INVENTION

1. Field of the Invention

This invention is in the field of disposable dental floss holders which have a strand of dental floss secured to one or more gripping elements which aid a user to position the strand of floss between adjacent teeth for flossing.

2. Relevant Prior Art

The prior art includes a great variety of such dental floss holders including Y and F shaped handles with floss extended between the ends of the top arms of the Y and between the ends of the fingers of the F respectively. In many of these devices the floss is permanently secured to handle as by molding in situ or by heating each end of the floss to form a bead that prevents the floss end from being pulled through the solid plastic of the holder. In alternative styles the floss is releasably attached to the handle so that it can be readily replaced if frayed or broken. Some holders have a floss supply on a spool within the handle or they may periodically receive a totally separate segment of floss from a source external of the handle.

The relevant prior art patents include U.S. Pat. Nos. 4,016,892; 4,006,750; 4,016,892; D 244,376; D 250,214; 5,086,792; 817,050; 4,403625; 3,696,821; 4,986,289; 3,799,177; 5,174,314 and 3,831,611 all incorporated herein by reference.

As these devices are usually mass produced in order to be manufactured economically, they are often designed to be aligned in production where a single strand of floss is continuous and contiguous between a plurality of dental floss holders, especially where the devices are injection molded and a strand of dental floss extends between a plurality of the devices.

A relatively newer prior art dental floss device consists of a pair of separate and independent gripping elements with a strand of dental floss extending between them. These gripping elements, are typically one half to one and a half inches long and have a variety of shapes including elongate, round, oval, flat, etc. Typically in mass production these devices are injection molded by aligning a plurality of devices with a single strand of floss extending contiguously between them. At the completion of the molding cycle and securing the floss ends to the handle or gripping elements the individual dental floss devices or units are cut from each other and readied for packaging.

In the latest described dental flossing device a pair of gripping elements is secured to ends of a strand of dental floss which extends freely and loosely between them, as it must for eventual use in flossing. However, between the time of initial manufacture and ultimate use these devices are collected, oriented, packaged individually or in groups, repackaged into shipping cartons, transported, stored and later displayed for sale.

A persistent problem that occurs with these devices is tangling and/or knotting of the floss, or random disorderly orientation of the units and floss and resulting unattractive or sloppy appearance of the product when the package is displayed or opened for use with the obvious negative impression and potentially negative impact on future sales.

A series of prior art patents to N. Charatan, U.S. Pat. Nos. 4,519,408; 4,836,227; 4,633,892 and 5,174,314 disclose oral hygiene devices including, for example, a strand of dental floss between a pair of gripping handles where the strand of floss is isolated by encasing it in a frangible tube. Upon breaking the tube into two parts, the floss is exposed and the parts become handles. The device of U.S. Pat. N0. 5,174,314 is relatively complex and expensive in that the strand of floss must have an enlarged mass on each end, all of which must be sealed within a tune which must have reduced diameter necks. The other Charatan devices are equally or more complex, expensive to manufacture and not suitable for the simple, highly economical mass production of the new invention disclosed herein.

An object of this invention is to provide a flossing device with separate gripping elements at opposite ends of a strand of dental floss where the floss is maintained straight before packaging and while packaged, until the device is ready for use.

A further object is to provide a dental flossing device where the two gripping elements are temporarily joined in a structure that holds the strand of floss in an extended state, the two gripping elements being easily breakable apart and separated from each other by the user.

A still further object is for the gripping elements to be generally elongated and joined such that their confirmed length approximates the length of the floss and thus maintains the floss in a straight line until the gripping elements are broken apart from each other.

Another object is to provide a choice of gripping elements that may be a pair of identical elements or a set of different elements.

A further object is to include a pointed projection on at least one of the elements for use as a toothpick and/or gum stimulator.

Another object is to provide a frame which holds and maintains the gripper elements spaced apart with the floss extended between them, where the elements are breakable apart from the structure to render the set of elements and included floss freely flexible between them. Also, this structure may include a toothpick like projection.

An additional object is to provide a flossing unit where the flexible floss is maintained in a straight line, and the three elements, namely two grippers and the included floss are maintained as a fixed-shape unit that is easily and speedily handled during and after packaging.

Another object is to provide a flossing unit that can be moved, oriented and positioned in packages without dangling or tangling and thus can more easily be kept clean.

These and other objects are achieved with this invention as summarized and later described in detail below.

SUMMARY OF THE INVENTION

This invention provides a dental flossing device having a strand of dental floss with a gripping element secured to each end of the floss, and means for maintaining these gripping elements in fixed spatial relationship relative to each other with the floss extended generally linearly therebetween, said means for maintaining these gripping elements being breakable whereby said elements are freely movable relative to each other and said floss is freely extendible or bendable between them.

The invention includes frangible junction means joining the two gripping elements which may be a tiny bridge or neck therebetween or the junction means may also be a frame that engages the two gripping elements and maintains them spaced apart from each other, each gripping element being breakable apart from the frame while ends of the floss remain attached to the gripping elements.

In the various embodiments the floss is maintained generally straight by the fixed assembly of components until a user breaks the gripping elements free of each other or free of the frame. The floss and gripping elements being positionally fixed with respect to each other provides a structure that is easily transportable, packaged, stored and displayed, without danger of the floss of each device becoming tangled in itself or tangled with floss or gripping elements of other flossers. This is especially useful for these flossing devices as they are fed to packaging machinery for either single or multi unit packages.

As known from my prior patent U.S. Pat. No. 4,016,892 flossing devices of the type discussed herein provide an improved tool and technique for cleaning food particles and plaque from between and on the surface of the teeth. The floss after insertion between two adjacent teeth can be maintained generally straight while it is moved up and down or less taut floss can be partially wrapped about a tooth before and during such movement. The gripping elements allow the user to easily, comfortably and securely hold onto the ends of the floss while it is being manipulated.

DETAILED DESCRIPTION OF THE PREFERRED EMBODIMENTS

FIGS. 1 and 2A–2D show a first embodiment 10 of the new Snap 'N Floss dental flossing device of the present invention. The device comprises a pair of elongated, generally flat gripping elements or grippers 12 which are each one to two inches in length, positioned end-to-end and joined by a neck or bridge 14. These elements and bridge are contiguous, with the bridge junction strong enough to maintain the gripping elements in the position and orientation shown unless and until the user bends or inclines one element relative to the other until these elements break apart at the bridge which is substantially weaker than the elements themselves.

Figure 1:
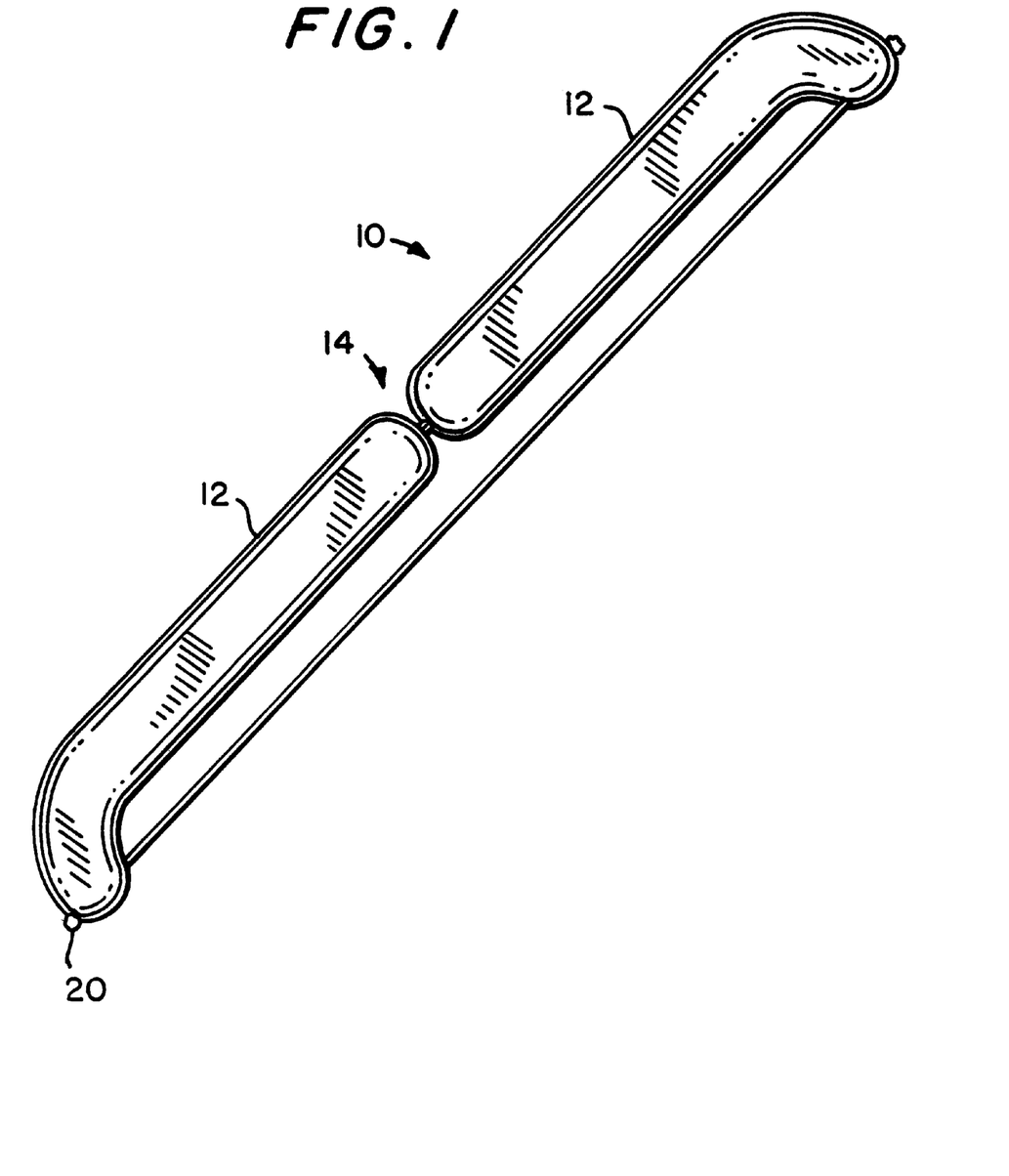
FIG. 1 is a top perspective view of a first embodiment of my new dental floss device.
Figure 2A:
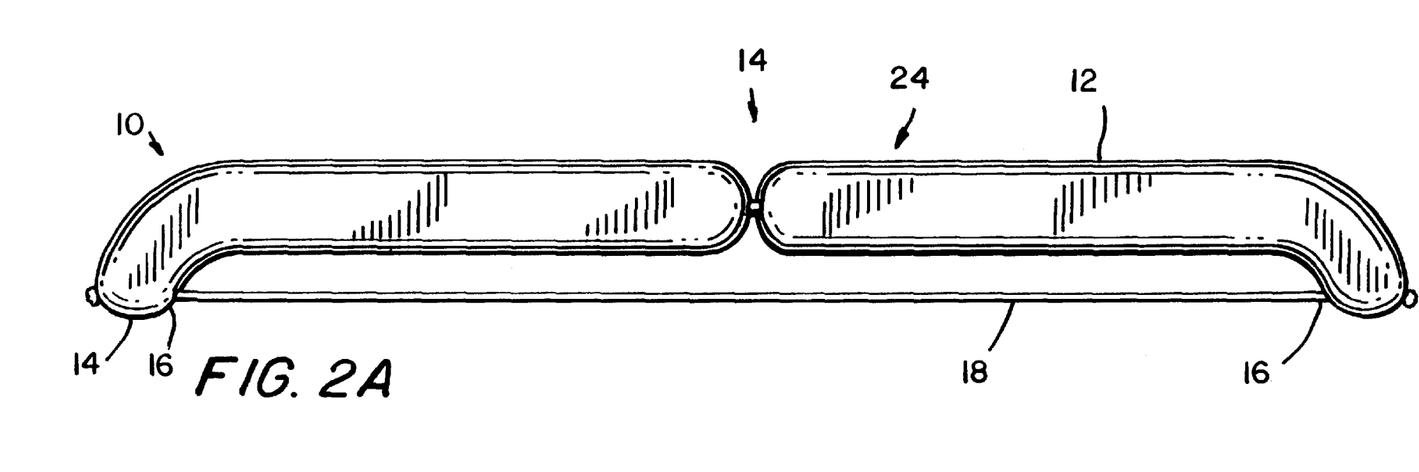
FIG. 2A is a top plan view thereof, the bottom plan view being a mirror image thereof.
Figure 2B:
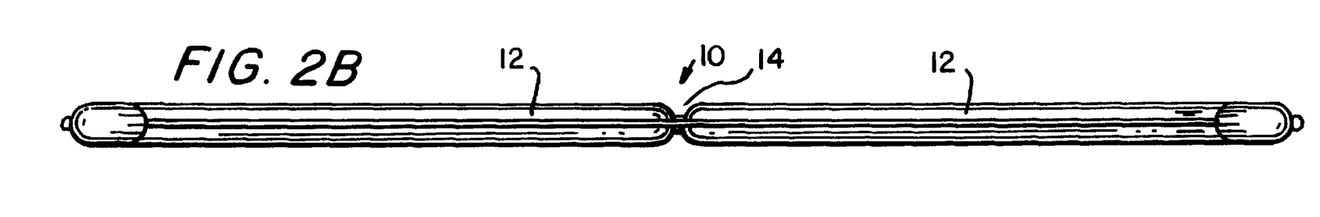
FIG. 2B is a front elevation view thereof.
Figure 2C:
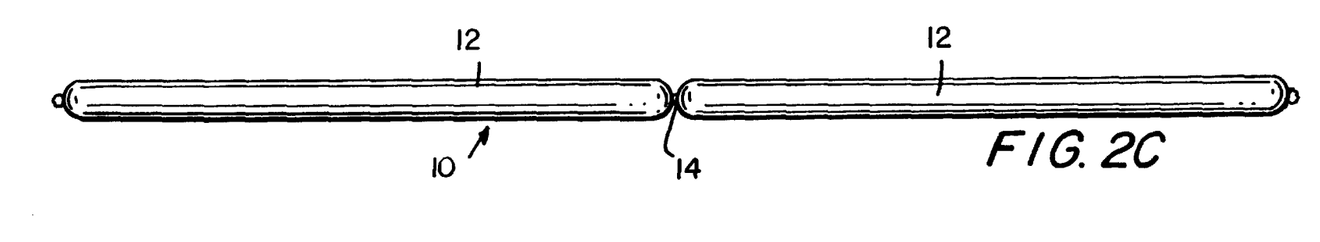
FIG. 2C is a rear elevation view thereof.
Figure 2D:
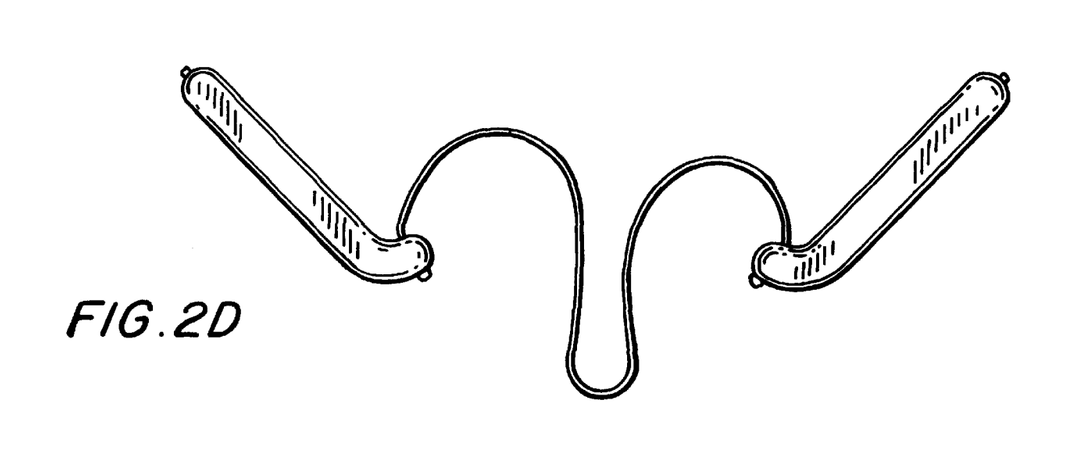
FIG. 2D is top plan view of this device with the gripping elements broken apart from each other.
Figure 2E:
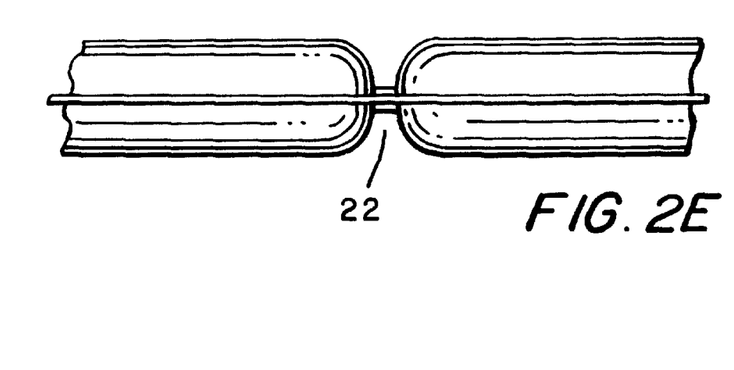
FIG. 2E is a fragmentary enlarged view of FIG. 2B.

The remote opposite ends 14 of the joined gripping elements 12 each engage one end 16 of a strand of dental floss 18. Typically these floss ends 16 are molded in situ into the gripper ends 14 by well known injection molding processes. For additional security of this engagement each exposed end 20 of the floss which extend outward and beyond the gripper end is heated or burned until its fibers coalesce into beads having diameter as a group greater than the diameter of the original floss and therefore greater than the diameter of the bore in the end of the gripper through which the floss extends.

The combination of grippers 12 and bridge or junction 14 establishes a composite elongate structure which maintains the strand of floss 18 essentially straight. This prevents each strand from becoming tangled or knotted in itself or with any other device. This is most advantageous immediately following molding when the floss devices are separated from each other and before, during and after packaging. This design and arrangement overcome a major problem in prior flossers, namely tangling of hundreds of loose flosser units, and the associated problem of these strands becoming dirty through handling and untangling.

For reasons of obvious cleanliness and convenience of handling, storing, shipping, display and sale, these flossing units need to be contained in closed and preferably at least partially transparent packages. Whether they are packaged as single units or in groups of two, three, five, ten, etc., the fact that each device has a stable, elongate shape with the floss extended generally axially renders every stage of packaging, storage, transport, display and sale easier, more efficient and more economical.

A user of this product, regardless of its many embodiments, needs only to remove it from any external packaging and to grasp and twist or bend the opposite gripping elements until the bridge portion breaks, or to bend and break other relevant parts until the grippers separate. In preferred embodiments the bridge portion breaks cleanly such that the exposed edges of the adjacent near ends of the grippers are relatively smooth or at least free of objectionable projections or burrs. After this breakage of the bridge the gripping elements hang freely at opposite ends of floss, and the strand of floss can be manipulated between pairs of adjacent teeth in the usual manner, with the gripping elements providing the usual convenience over the original style of wrapping ends of the floss around the users' fingers.

A typical flosser of the type described above is made of polystyrene, polypropylene or nylon for the gripping elements and PTFE, nylon or polyethylene for the dental floss. The gripping elements when positioned end-to-end and joined have total length of about 2⅜" and thickness of about 1/16", and with the bridge having width of about 0.040 inches, thickness of about 0.020 inches and length of 0.10 inches. With these dimensions the bridge when bent will break with a snap, thus the commercial name Snap 'N Floss.

Figure 3:
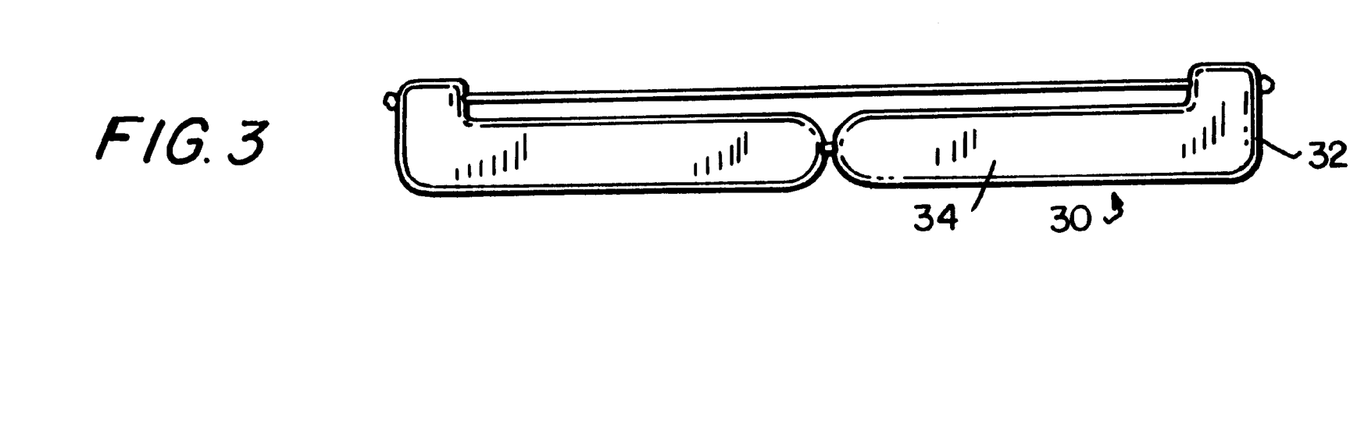
FIG. 3 is a top plan view of a second embodiment thereof.

The present invention may take a great variety of forms, as generally exemplified by FIGS. 3 to 11 which show a few additional preferred embodiments. FIG. 3 shows a second embodiment flossing device 30 similar to that of FIG. 2A except that the remote ends 32 of the gripping elements 34 are generally rectangular.

Figure 4:
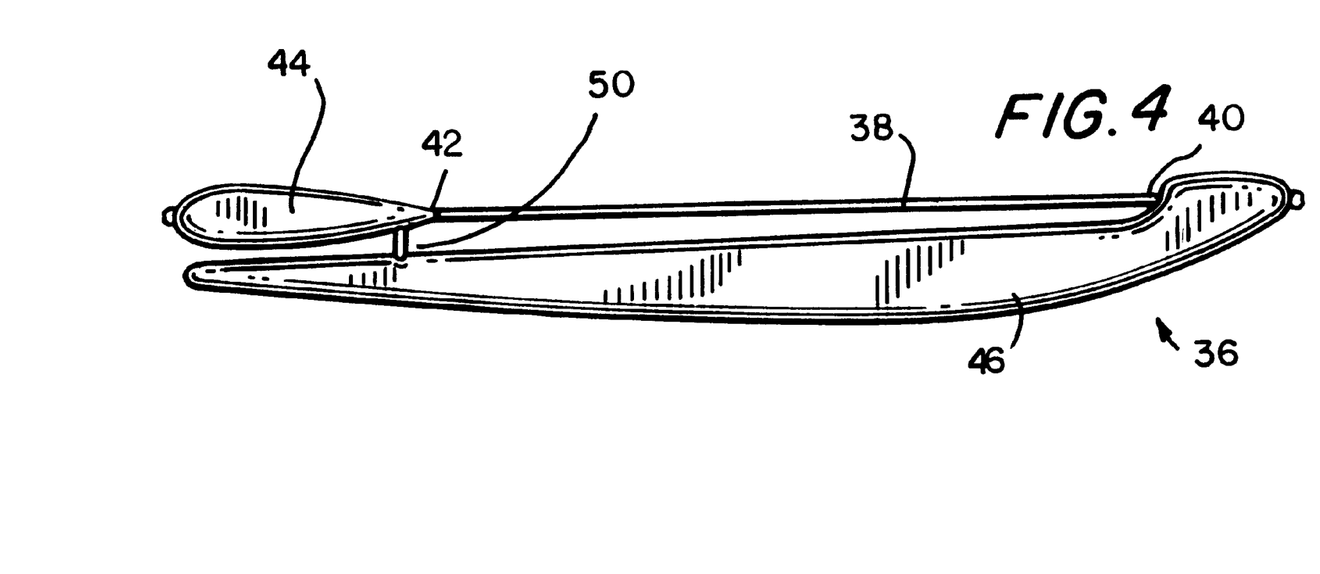
FIG. 4 is a top plan view of a third embodiment thereof.

FIG. 4. shows a third embodiment flossing device 36 where the strand of floss 38 is maintained generally straight and extended by connection of its ends 40, 42 to a set of two dissimilar gripping elements 44, 46. In this embodiment element 44 is smaller than the basic gripper of FIG. 1, but still adequate to be easily gripped, and element 46 is far longer terminating in a pointed tip 48 which is usable as a toothpick or gum stimulator pick. As with the FIGS. 1–3 embodiments, the two gripping elements are joined by bridge 50 which will readily break or snap apart when bent.

Until such breaking the bridge maintains elements 44 and 46 in their elongated positional relationship which holds the floss straight and secure. These gripping elements have the same general thickness as in the prior embodiments so that the resulting arrangement and package is relatively flat. Also, the bridge section is similar in size and relative strength so that it readily snaps apart when bent.

Figure 5A:
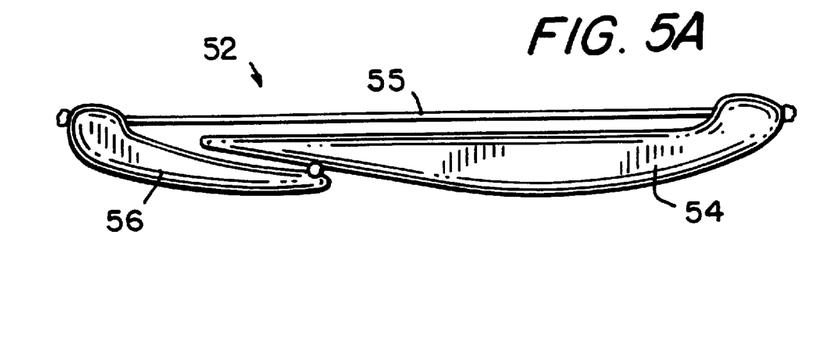
FIG. 5A is a top plan view of a fourth embodiment thereof.
Figure 5B:
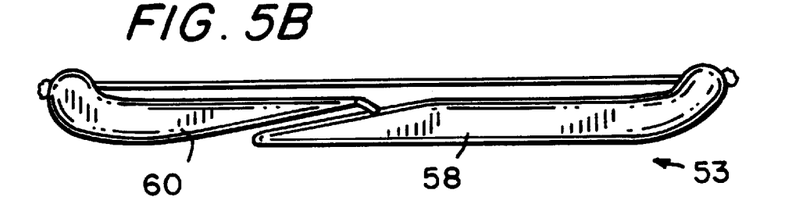
FIG. 5B is a top plan view of a fifth embodiment thereof.
Figure 5C:
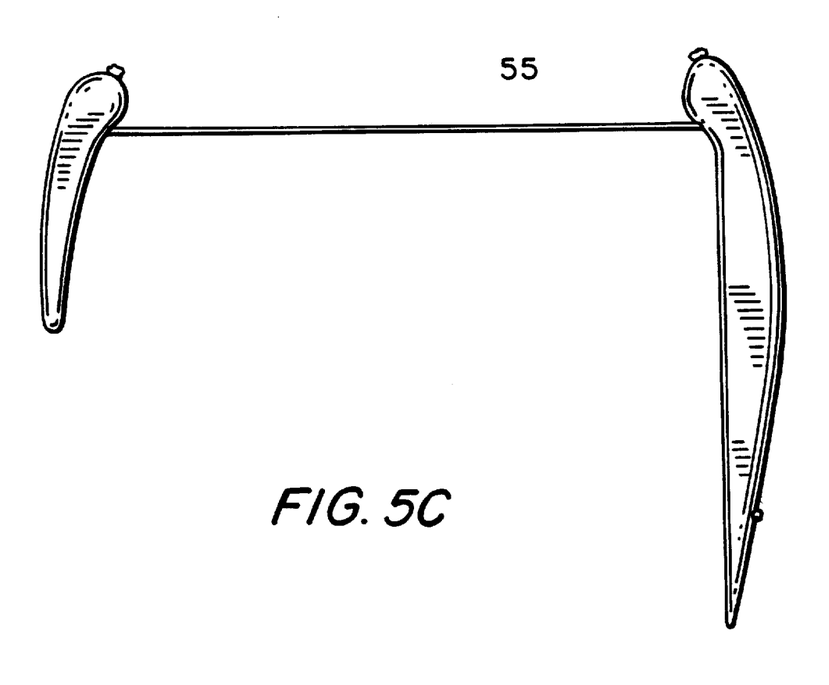
FIG. 5C is a top plan view of a fifth embodiment shown with gripping elements broken apart.

FIGS. 5A and 5B show further embodiments 52, 53 generally similar to that of FIG. 4 with a very long pointed gripping element 54 which is usable as a toothpick and a short pointed element 56 in device 52 and slightly different long and short elements 58, 60 in device 53. FIG. 5C shows the device of FIG. 5B with elements 54 and 56 broken apart and floss 55 extending freely between these elements.

Figure 6:
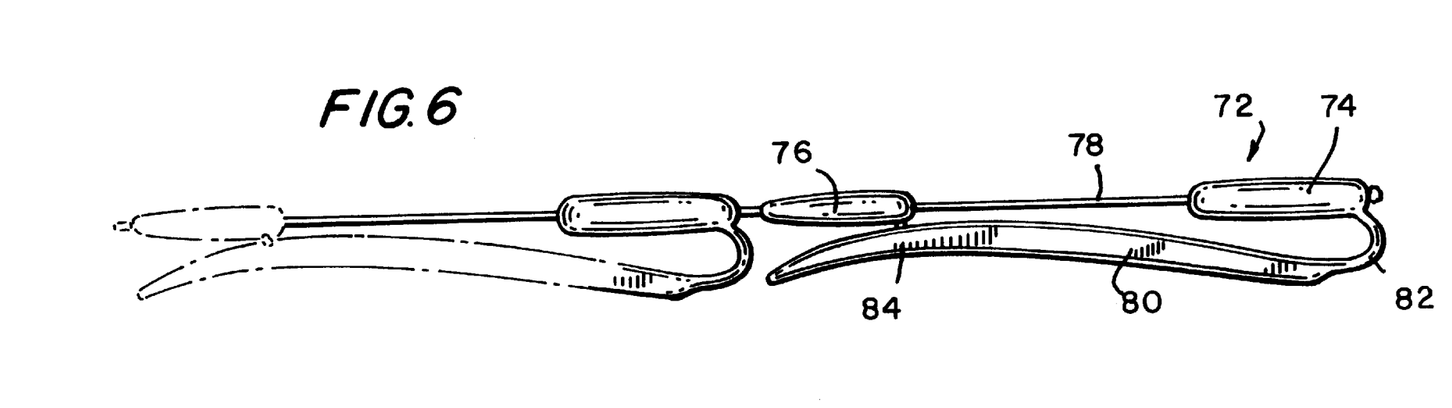
FIG. 6 is a top plan view of a sixth embodiment thereof.
Figure 7:
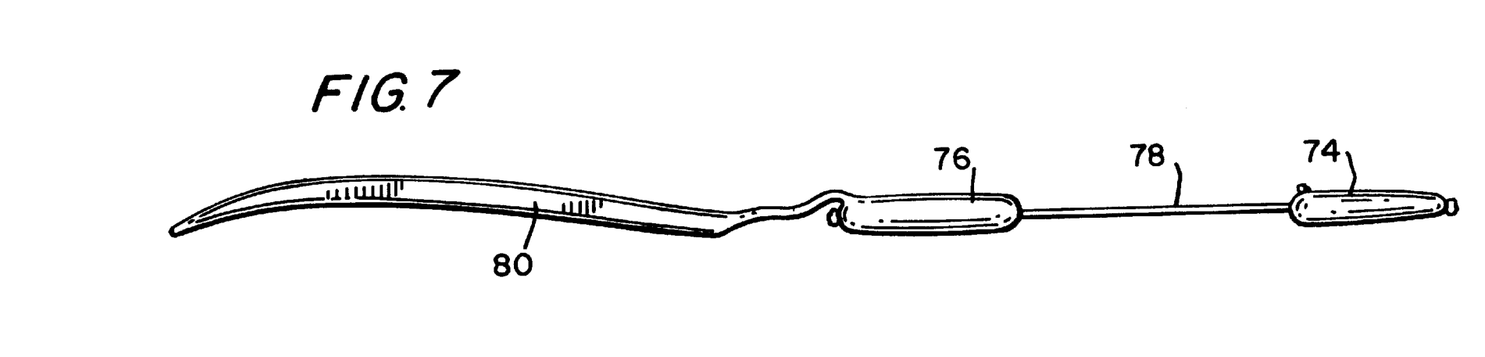
FIG. 7 is a top plan view of the sixth embodiment in unfolded state.

FIGS. 6, 7, show a still further embodiment 72 where two relatively small gripping elements 74, 76 are maintained apart with floss 78 held straight between them by the very long pick/stimulator 80 joined to the element 74 by a flexible neck 82 and joined to element 76 by a frangible bridge 84. FIG. 7 merely shows the device of FIG. 6 with bridge 84 broken, part 80 fully extended, and floss 78 extending freely between elements 74, 76.

Figure 8:
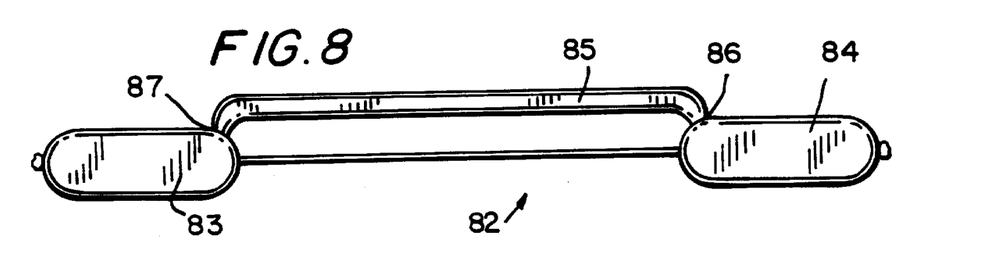
FIG. 8 is a top plan view of the seventh embodiment.

FIG. 8 shows a further embodiment 82 where the gripping elements 83, 84 are maintained apart by a relatively thin bar or bridge 85 joined to the elements by frangible connections 86, 87. In this version the two frangible connections must be broken to release the gripping elements and floss therebetween; however, the assembly remains simple to make and use and is effective for its intended purpose.

Figure 9:
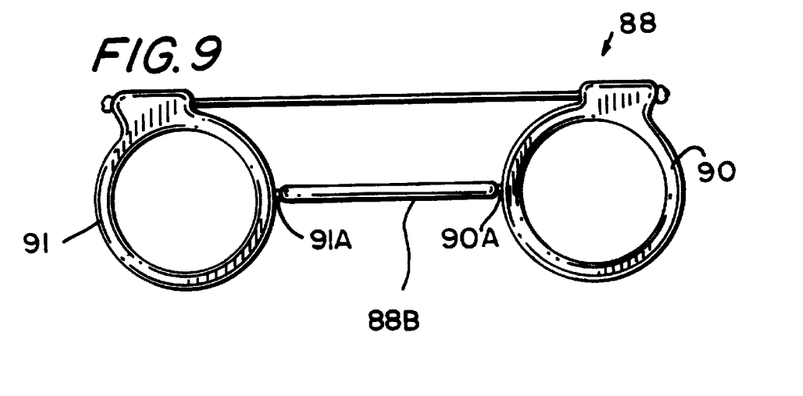
FIG. 9. Is a top plan view of the eighth embodiment.
Figure 10:
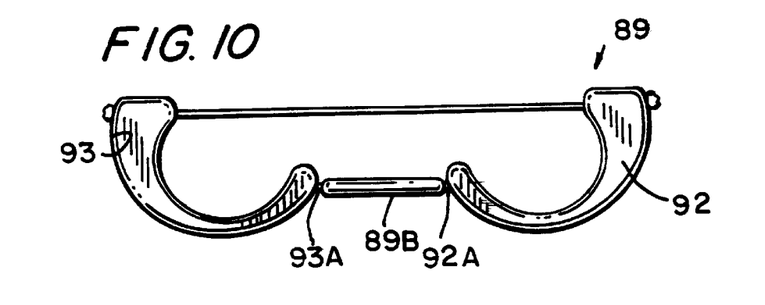
FIG. 10 is a top plan view of the ninth embodiment.
Figure 11:
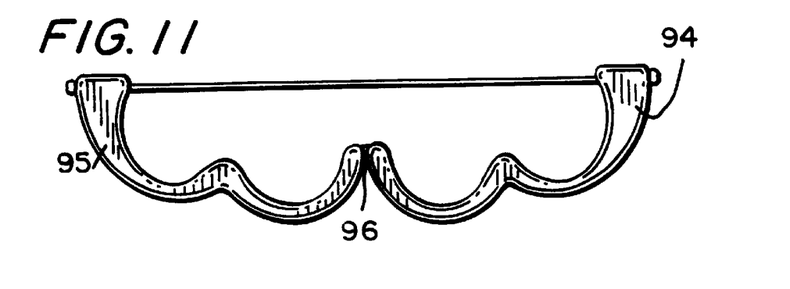
FIG. 11 a top plan view of the tenth embodiment.

FIGS. 9 and 10 show further embodiments 88, 89 which use two bridge means 88B, 89B respectively as in FIG. 8. FIG. 9 has ring elements 90, 91 and frangible connections 90A, 91A respectively. FIG. 10 has arch-like gripping elements 92, 93 and frangible connections 92A, 93A respectively. FIG. 11 has double arch gripping elements 94, 95 joined by a single frangible connection 96. All of the above-mentioned frangible connections are readily broken by simple bending.

While all the embodiments shown are injection molded into relatively flat, thin gripping elements, and a flat, thin assembly for ease of packaging, storage, transport and display, many other shapes of gripping elements and methods of floss attachment are possible within the spirit and scope of this inventions.

Also, within the overall concept of this invention is the concern for mass production manufacture of these devices. For all the dental flosser devices shown it is contemplated that they may be injection molded in multi-cavity molds where each strand of dental floss extends through a plurality of aligned cavities. At the completion of hardening the plurality of molded assemblies are cut apart from each other, and the exposed ends of floss are heated or burned to form the beaded ends that help prevent the floss from later being pulled out of the gripper elements.

It is understood that variations, modifications and substitutions may be made in the foregoing that will be apparent to those skilled in the art, it being intended that the scope of the invention will be defined by the appended claims.

I claim:

1. A disposable dental flossing device comprising
a set of gripping elements, each having a body part and an outer surface thereof, at least one of said gripping elements being elongated and having a length dimension,
a strand of dental floss having length L and opposite ends, each of said ends fixedly secured to one of said griping elements, and connecting means permanently engaging and maintaining said pair of gripping elements in fixed spatial relationship with respect to each other as a single contiguous device with said strand extending in a generally straight line external of said outer surfaces of said gripping elements and extending lengthwise generally parallel to said length dimension of said at least one elongated gripping element,
said connecting means being breakable whereby said gripping elements become separated from each other while each gripping element remains secured to said one end of said strand.

2. A dental flossing device according to claim 1 wherein each gripping element has near and far ends, said near ends respectively are joined by said connecting means, and said ends of the dental floss are secured to said far ends of the gripping elements which far ends are thus spaced apart a distance of said length L.

3. A dental flossing device according to claim 1 wherein each of said gripping elements is generally flat and has length of about 1 1/14 inches, width of about 1/8 to 1/4 inch, and thickness of about 1/16–1/8 inch and said connecting means has thickness of about 1/32 inch.

4. A dental flossing device according to claim 1 wherein said floss is multifilimented ultrahigh molecular weight polystyrene.

5. A dental flossing device according to claim 1 wherein said gripping elements are polystyrene and said dental floss is multifilimented ultra high molecular weight polystyrene.

6. A dental flossing device according to claim 2 wherein said gripping elements are generally flat and when connected define a generally planar structure.

7. A dental flossing device according to claim 2 wherein said connecting means has thickness substantially less than the thickness of the gripping elements.

8. A dental flossing device according to claim 7 wherein said gripping elements and said connecting means are contiguous injection molded plastic.

9. A dental flossing device according to claim 8 wherein said connecting means has thickness of about 1/32 inch.

10. A dental flossing device according to claim 2 wherein each gripping element has length of about one inch.

11. A dental flossing device according to claim 2 wherein each gripping element has a generally J or L shape comprising a stem having top and bottom parts and a foot extending transversely from said bottom part, and wherein the top part of the stem comprises said near end of each gripping element and the foot comprises said far end of each gripping element.

12. A dental flossing device according to claim 11 wherein said ends of said dental floss are molded in situ into said far ends of said gripping elements.

13. A dental flossing device according to claim 2 wherein said gripping elements and said connecting means are contiguous injection molded plastic.

14. A dental flossing device according to claim 13 wherein said connecting means has thickness substantially less than the thickness of said gripping elements.

15. A set of dental flossing devices of claim 12 comprising at least two of said dental flossing devices situated end-to-end with said dental floss of each dental flossing device being part of a single continuous generally linear strand.

16. A dental flossing device according to claim 2 wherein each of said gripping elements is elongated and curved.

17. A dental flossing device according to claim 2 wherein said ends of said dental floss are molded in situ into said far ends of said gripping elements.

18. Apparatus according to claim 1 wherein one of said gripping elements has a far end that is tapered to form a toothpick.

19. A device according to claim 1 wherein both of said gripping elements have length dimensions and both while they are connected are situated in end-to-end relationship.

20. A device according to claim 19 wherein both of said gripping elements are elongated.

21. A device according to claim 19 wherein each of said gripping, elements has an elongated body part and opposite proximal and distal ends, said proximal ends of said two gripping elements being connected together, said distal ends extending transversely of said body parts.

22. A device according to claim 21 wherein said connected gripping elements define a U-shape with said body parts forming the base of the U and said transversely extending distal ends forming the legs of the U.

23. A device according to claim 1 wherein said at least one elongated gripping element is substantially longer than the other of said gripping elements.

24. A disposable dental flossing device comprising a set of gripping elements, each having a body part and an outer surface thereof, each having a length dimension and opposite ends, a strand of dental floss having length L and opposite ends, each of said ends of said strand being fixedly secured to one of said gripping elements, and connecting means permanently engaging and maintaining said set of gripping elements in fixed spatial relationship with respect to each other in an end-to-end relationship establishing a lengthwise dimension with said strand having its length L extending in a generally straight line external of said outer surfaces of said griping elements and extending lengthwise of said length dimension of said end-to-end gripping elements, said connecting means being breakable, whereby said gripping elements become separated from each other while each griping element remains secured to said one end of said strand.

25. A dental flossing device comprising a set of gripping elements a strand of dental floss having length L and opposite ends, each end fixedly secured to one of said gripping elements, and bridge means maintaining said gripping elements spaced apart and said dental floss extending generally lineraly between said gripping elements said bridge means engaging each of said gripping elements in a frangible connection until said frangible connections are broken, whereby said floss may hang freely between said gripping elements while said ends of the floss remain secured to said gripping elements.

* * * * *